(12) United States Patent
Psarrakis et al.

(10) Patent No.: US 12,213,954 B2
(45) Date of Patent: Feb. 4, 2025

(54) COLCHICINE SOLUTION

(71) Applicant: PHARMA-DATA RESEARCH AND DEVELOPMENT SINGLE MEMBER S.A., Lavrio (GR)

(72) Inventors: Ioannis Psarrakis, Lavrion (GR); Konstantinos Lioumis, Lavrion (GR)

(73) Assignee: PHARMA-DATA RESEARCH AND DEVELOPMENT SINGLE MEMBER S.A., Lavrio (GR)

( * ) Notice: Subject to any disclaimer, the term of this patent is extended or adjusted under 35 U.S.C. 154(b) by 0 days.

(21) Appl. No.: 18/681,394

(22) PCT Filed: Aug. 8, 2022

(86) PCT No.: PCT/EP2022/072274
§ 371 (c)(1),
(2) Date: Feb. 5, 2024

(87) PCT Pub. No.: WO2023/012374
PCT Pub. Date: Feb. 9, 2023

(65) Prior Publication Data
US 2024/0277638 A1 Aug. 22, 2024

Related U.S. Application Data

(60) Provisional application No. 63/262,070, filed on Oct. 4, 2021.

(30) Foreign Application Priority Data

Aug. 6, 2021 (NL) ..................................... 2028937

(51) Int. Cl.
*A61K 31/165* (2006.01)
*A61K 9/08* (2006.01)
*A61K 47/10* (2017.01)
*A61K 47/12* (2006.01)
*A61K 47/14* (2017.01)
*A61K 47/36* (2006.01)
*A61K 47/38* (2006.01)

(52) U.S. Cl.
CPC .............. *A61K 31/165* (2013.01); *A61K 9/08* (2013.01); *A61K 47/10* (2013.01); *A61K 47/12* (2013.01); *A61K 47/14* (2013.01); *A61K 47/36* (2013.01); *A61K 47/38* (2013.01)

(58) Field of Classification Search
CPC ........ A61K 31/165; A61K 9/08; A61K 47/10; A61K 47/12; A61K 47/14; A61K 47/36; A61K 47/38
See application file for complete search history.

(56) References Cited

U.S. PATENT DOCUMENTS 9,907,751 B2  3/2018  Muni et al.

FOREIGN PATENT DOCUMENTS

CN  110448527 A  11/2019
WO  2017156392 A1  9/2017

*Primary Examiner* — Matthew P Coughlin
*Assistant Examiner* — Quincy McKoy
(74) *Attorney, Agent, or Firm* — FISHERBROYLES, LLP; Roger L. Browdy

(57) ABSTRACT

Described is a stable buffered aqueous colchicine solution or suspension being free of benzyl alcohol, comprising colchicine, a water miscible solvent and a preservative, characterized in that the solution comprises 0.01-1.0 w/v % colchicine, 2.5-15.0 w/v % glycerol and 0.05-1 w/v % preservative, the pH of the solution or suspension being 4.5-7.0. A method for the preparation thereof is also disclosed.

21 Claims, No Drawings

COLCHICINE SOLUTION

The invention relates to a stable buffered aqueous colchicine solution or suspension being free of benzylalcohol.

Colchicine or acetyltrimethylcolchicine (CAS 64-86-8) is a complex α-tropolone derivative. Pure colchicine has yellow needle-like crystals with a melting point of 157° C. It is well soluble in water, ethanol and chloroform, and has a bitter taste.

The systematic name of colchicine is (S)—N-(5,6,7,9-tetrahydro-1,2,3,10-tetramethoxy-9-oxo-benzo[a]heptalene-7-yl)acetamide with the following chemical structure:

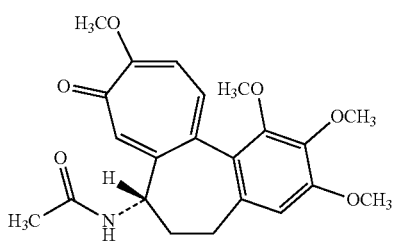 [SMILES: COc1cc2c(c(OC)c1OC)-c1ccc(OC)c(=O)cc1[C@@H](NC(C)=O)CC2]

Colchicine is an alkaloid from the autumn crocus (*Colchicum autumnale*), which is effective against gout. Colchicine can inhibit mitosis, destroy the spindle, and arrest the chromosomes in the mid-division. The cell does not divide and resulting in doubling the chromosomes. For this reason, the substance is used in plant breeding to produce polyploid plants. In the past, it was also used in the treatment of cancer. At present, only the derivative demecolcine is used for this purpose, and only sporadically. Colchicine is also found in the climbing lily (*Gloriosa superba*), even in a higher concentration than in the autumn crocus, but the plant is difficult to propagate, rendering it impossible to use for colchicine production profitably.

In drug applications, colchicine inhibits the production of interleukin 6 in local cells, so as to control local pain, swelling and inflammation in the joints. The pharmacological effect of colchicine for gout symptoms is mainly to reduce the activity of white blood cells and phagocytosis and reduce the formation of lactic acid, thereby reducing the deposition of uric acid crystals, reducing the inflammatory response of gout inflammation in patients, and having an analgesic effect.

Colchicine preparations have been sold internationally since the 1960s and are currently in solid forms such as tablets and capsules. However, for gout patients, gout attacks and other causes of dysphagia make some patients unable to get immediate effects from solid preparations.

Aqueous oral liquid colchicine formulations are known. U.S. Pat. No. 9,907,751 describes such a formulation comprising 0.012 w/v % colchicine, 0.3 w/v % benzyl alcohol, a 10 w/v % 1:1 mixture of glycerine and propylene glycol, xanthan gum, a buffer, a sweetener, and a flavour. Stability of the solution is obtained by the presence of xanthan gum. The product is marketed under the brand name Glopebra.

Benzyl alcohol is used as a bacteriostatic preservative. However, it is not suitable for young children. In addition, a number of toxic effects are known, including respiratory problems, vasodilatation, low blood pressure, cramps and paralysis.

A benzyl alcohol free oral colchicine solution is known from CN110448527, wherein the use of benzyl alcohol is avoided. Instead, a mixture of methylparaben and propylparaben is used. Instead of xanthan gum as thickener, hydroxypropyl cellulose is used. The colchicine solution of CN110448527 further comprises propylene glycol as solvent.

Propylene glycol is also not well tolerated by young children (European Medicines Agency assessment Report, EMA/175205/2014) and should therefore preferably be avoided.

It has now been found that an aqueous oral colchicine solution or suspension can be obtained, that is free of benzyl alcohol, with improved stability and that is also suitable for administration to small children. To this end, the invention provides a buffered aqueous colchicine solution or suspension being free of benzyl alcohol, comprising 0.02-1.0 w/v % colchicine, 2.5-15.0 w/v % glycerol and 0.05-1 w/v % preservative, the pH of the solution or suspension being 3.5-7.0.

It has been found that the presence of glycerol in the composition results in a stable colchicine solution without the need to include benzyl alcohol. It has also surprisingly been found that the solution can be void of an antioxidant and of a thickener. The absence of a thickener allows sterilisation by filtration facilitating industrial production.

The term 'buffered' means that the composition comprises a buffer system capable of buffering the pH of the solution in the envisaged range of 4.5-7.0. The skilled person is aware of suitable buffer systems. Herein, when it comes to colchicine, the term 'solution' also encompasses suspensions, unless otherwise indicated. The term 'composition' in this respect comprises both colchicine solutions and suspensions Colchicine solutions, known in the art have a colchicine content of 0.12 mg/ml, i.e. 0.012 w/v %. It has attractively been found that the solution of the present invention can comprise up to 0.30 mg/ml while still being stable after several months at incubation conditions of 40° C. or even higher. In an attractive embodiment, the solution therefore comprises 0.02-0.03 w/v % colchicine. In another embodiment, the solution comprises 0.022-0.030 w/v % colchicine, preferably 0.24-0.26 w/v %, and more preferably 0.025 w/v % colchicine. Colchicine can be in the form of the colchicine base or a salt, solvate, derivative or solvate thereof.

The solution preferably comprises 5-10 w/v % or 5-12 w/v %, preferably 7-11 w/v %, more preferably 8-10 w/v, and most preferably 10 w/v % glycerol as water miscible solvent. At such glycerol concentrations, stable solutions are obtained.

It was found that when the solution comprises glycerol, improved stability is observed when compared with benzyl alcohol free colchicine solutions that do not have glycerol. The solution is preferably free of propylene glycol, most preferably free of any glycol.

The solution comprises 0.05-1 w/v % preservative. Attractively, the solution comprises 0.10-0.40 w/v % preservative. Although may preservatives are suitable, the preservative is preferably chosen from the group, consisting of methyl paraben, ethyl paraben, propyl paraben, butyl paraben, sorbic acid, potassium sorbate, and combinations thereof, the preservative preferably comprising methyl paraben or a combination of methyl and propyl paraben, in particular sodium methyl paraben. In order to provide a colchicine solution suitable for infants, the preservative preferably comprises methylparaben, is preferably void of propyl paraben, more preferably of any additional preservative. the preservative comprises in particular sodium methyl paraben.

The pH of the solution is in the acid to neutral range in order to be acceptable as a oral solution, e.g. for oral administration. The solution preferably has a pH of 4.5-6.5, more preferably 5.0-6.0, even more preferably 5.2-5.8, and most preferably 5.4-5.6. Further, the stability of the solution is higher at a pH of 6.0 or lower. Therefore, pH of the solution is preferably 6.0 or lower, more preferably 5.8 or lower.

In order to provide a stable pH, the solution is buffered, which means that the solution comprises a buffer system, in particular a pharmaceutically acceptable buffer system that comprises one or more pH buffering agents. The solution preferably comprises 0.05-2.0 w/v %, more preferably 0.5-1.0 w/v % buffering agent. Suitable buffer agents are known to the skilled person. Preferred buffer agents are chosen from the group, consisting of hydrochloric acid, acetic acid, ammonia solutions, monoethanolamine, diethanolamine, triethanolamine, meglumine, sodium citrate, citric acid, lactic acid, phosphoric acid, propionic acid, sulphuric acid, tartaric acid, potassium bicarbonate, potassium citrate, potassium hydroxide, sodium bicarbonate, sodium borate, and sodium hydroxide, or a combination of two or more thereof. The buffering agent preferably comprises citric acid and a citrate salt, preferably sodium citrate.

Although the solution of the invention may comprise a thickener agent, it has been found that in the presence of glycerol in amounts as defined herein, the stability is not improved by the presence of a thickener. As the presence of a thickener results in cumbersome production on industrial scale as sterile filtration is cumbersome, it is advantageous to include less thickener. To this end, the solution preferably comprises 0.25 w/v % or less thickening agent. Any pharmaceutically acceptable thickening agent known to the skilled person can be chosen, and is in particular chosen from the group, consisting of hydroxyethyl cellulose, hydroxypropyl cellulose, sodium alginate, sodium carboxy methylcellulose, gellan gum, xanthan gum, acacia, guar gum, locust bean gum, gum tragacanth, starch, carbopols, methylcellulose, polyvinylpyrrolidone, polyethylene oxide polymer and combinations thereof. The thickening agent preferably comprises hydroxyethylcellulose or xanthan gum. The amount of the thickening agent, if present, is preferably 0.1-0.2 w/v %. However, it was found that the stability even increases if the solution is free of thickener. Therefore, in a very attractive embodiment, the solution of the invention is free of a thickening agent.

Although the solution of the invention may comprise an antioxidant, it was found that the presence of an antioxidant does not significantly improve the stability of the solution. If incorporation of an antioxidant is envisaged, the stability of the solution should be tested as is was found that under rather harsh test conditions, solutions that comprises certain antioxidants had a limited stability. However, under normal storage conditions, the presence of an antioxidant does not hamper the stability at least not significantly. To this end, the solution of the invention can attractively comprise 1.0 w/v % or less antioxidant. Any pharmaceutically acceptable antioxidant known to the skilled person can be chosen. The antioxidant is preferably chosen from the group, consisting of butylated hydroxyl anisole, butylated hydroxyl toluene, tocopherol, ascorbyl palmitate, ascorbic acid, sodium metabisulfite, sodium sulphite, sodium thiosulfate, propyl gallate, and combinations thereof, the antioxidant preferably comprising sodium metabisulphite. The amount of the antioxidant, if present in the solution, is preferably 0.01-0.25 w/v %, more preferably 0.01-0.1 w/v %. It has surprisingly been found that the stability even increases if the solution is free of antioxidant. Therefore, in a very attractive embodiment, the solution of the invention is free of antioxidant.

In order to provide a solution with an acceptable taste, the solution preferably comprises a sweetening agent. Sweeting agents are known in the art, such as commonly known saccharides, such as sucrose, fructose, glucose, lactose. However, it is preferred for the solution of the invention to comprise an artificial non-sugar alcohol sweetening agent. Although sugar alcohols such as xylitol, mannitol, glycerol, erythritol, threitol, arabitol, ribitol, mannitol, sorbitol, galactitol, fucitol, iditol, inositol, volemitol, isomalt, maltitol, lactitol, maltotritol, maltotetraitol, and polyglycitol can be used in the solution of the invenit ion, a sugar alcohol may also have a thickener function. As described above, the presence of a thickener is less preferred, and for that reason, sugar alcohols having a thickener function are less preferred. An artificial non-sugar alcohol sweetening agent is an additive that provides sweet taste like that of sugar but derived through manufacturing of plant extracts or processed by chemical synthesis, not belonging to the sugar alcohols as described above. Such artificial sweeteners contain often far less energy than regular sugars used for sweetening. Such sweeteners can also be referred to as 'non-nutritive sugar-based sweeteners', i.e. having no significant nutritional value and not sugar based. Herein, a chemically treated sugar is an artificial sweetener. For example, sucralose is produced by controlled chlorination of the sugar saccharose. Sucralose is therefore an artificial sweetener, that is derived from a sugar, but the sweetener is defined herein as 'non-sugar based'. Artificial non-sugar alcohol sweeteners do not have the thickening effect of sugar alcohol and have a significantly higher sweetening power.

Because of the high sweetening power of artificial non-sugar alcohol sweetening agents, it has become possible to provide for a composition wherein the off-taste of the colchicine is sufficiently masked, while retaining a workable volume of the composition, without the presence of a significant amount of sugar alcohol, while also achieving acceptable shelf stability.

The amount of sweetening agent is preferably chosen such, that it corresponds with the sweetening power in the solution of 20-500 w/v % saccharose. This means that, e.g., in case sucralose is used as the sole artificial sweetening agent, the amount of sucralose is 0.033-0.83 w/v %, as the sweetening power of sucralose is 600 times that of saccharose. More preferably, the amount of non-sugar alcohol sweetening agent in the solution has a sweetening power that corresponds with the sweetening power of 40-200 w/v % saccharose.

Optionally, other pharmaceutically acceptable water miscible solvents can be used together with glycerol, in particular selected from the group consisting of: polyols, such as alkane triols, alkane diols and polyethylene glycol; alcohols, such as ethanol, isopropyl alcohol; acetone, phthalates, such as dibutyl phthalate, diethyl phthalate, dimethyl phthalate; dimethyl sulfoxide, dimethylacetamide, glycofurol, isopropyl myristate, isopropyl palmitate, propylene carbonate, pyrrolidine, glycerine triacetate, triethyl citrate, triolein, or a combination of two or more thereof. If one or more additional water miscible solvents are present in the solution, the ratio thereof with glycerol is preferably 1-5:10 glycerol. It is preferred to have a high relative glycerol content as compared to the one or more additional water miscible solvents, and preferably, glycerol is the sole water miscible solvent present in the colchicine solution.

In order to increase the attractivity of the solution even more, in particular for infants and young children, the solution comprises a flavouring agent. At acid or neutral pH as for the solution of the invention, the majority of commonly known flavouring agents can be used. The flavouring agent is preferably chosen from the group, consisting of forest fruits flavour, grapefruit, orange, lime, lemon, mandarin, pineapple, strawberry, raspberry, mango, passion fruit, kiwi, apple, pear, peach, apricot, cherry, grapes, banana, cranberry, blueberry, black currant, red currant, gooseberry, lingonberries, cumin, thyme, basil, chamomile, valerian, fennel, parsley, camomile, tarragon, lavender, dill, bergamot, salvia, aloe vera balsam, spearmint, peppermint, eucalyptus, and combinations of two or more thereof, the flavour preferably comprising orange or strawberry flavour. The solution preferably comprises 0.01-1.0 w/v % more preferably 0.05-0.5 w/v % flavouring agent.

For practical and commercial use, the solution of the invention will have at least 18 months, preferably at least 24 months shelf life. Preferably, the colchicine solutions are stable at room temperature and do not require refrigeration. Aqueous colchicine solutions or suspensions of the invention therefore preferably comprise at least 95% colchicine after 24 months storage at 25° C. at a relative humidity of 60%, preferably at least 96%, more preferably at least 97%, even more preferably at least 98% and most preferably at least 99% as compared to the amount of colchicine at the beginning of the storage.

Preferably, the colchicine solution comprises:
a. less than 1.2%, preferably less than 1.1 total impurities after 6 months storage at 5° C. at a relative humidity of 60%, and/or
b. less than 1.2%, preferably less than 1.1% total impurities after 6 months storage at 25° C. at a relative humidity of 60%, and/or
c. less than 1.2%, preferably less than 1.1% total impurities after 6 months storage at 30° C. at a relative humidity of 65%, and/or
d. less than 1.4%, preferably less than 1.3%, more preferably less than 1.2% and most preferably less than 1.1% total impurities after 5 months storage at 40° C. at a relative humidity of 75% and/or
e. less than 1.4%, preferably less than 1.3% total impurities after 6 months storage at 40° C. at a relative humidity of 75%.

The invention also relates to a method for the preparation of a solution of the invention, comprising the steps of:
(i) mixing colchicine and purified water,
(ii) admixing the preservative agent,
(iii) admixing the pH buffering agents
(iv) admixing the glycerol,
(v) if necessary, adjust the pH by addition of a pH buffering agent,
(vi) if necessary, adjust the final volume by adding from the rest of the water of step (i),
(vii) optionally, filter through 1 to 10 μm pore sieve, and
(viii) filling in an appropriate light protected container.

As colchicine is light sensitive, at least step (i) of the method is preferably performed under light protected conditions. This can be accomplished by preforming the step or method in the dark, or by using a container that protect the contents from light. Additional components, such as those as described above can be added as part of, during or between one or more of the above steps (i)-(viii). In case an additional water miscible solvent is used, it is preferably added in step iv).

For examples, the sweetener, if present, is preferably added in step (iii) or between steps (iii) and (iv), and, if present, flavour, thickening agent and/or antioxidant are added in step (iii) or between steps (iii) and (iv) or after step (iv). The flavouring agent is preferably added after glycerol is added.

EXAMPLES

As colchicine may degrade under the influence of light, the process was performed shielded from direct sunlight. The process was otherwise performed using regular manufacturing equipment. The basic steps are as follows:

Materials and Methods

Preparation of Colchicine Solutions Compositions
The following ingredients were used in the preparations described below:
Colchicine (Sarv Labs, India; Indena, Italy);
Sweetener: Sucralose (Nutrilo, Germany)
Orange flavour (Symrise, Germany)
Methyl paraben sodium (Emprove®, Merck, US)
Propyl paraben sodium (Clariant, Germany)
Hydroxyethylcellulose (Natrosol 250 HX®, Ashland, US)
Xanthan Gum (Jungbunzlauer, Switzerland)
Citric acid anhydrous (Citrique Belge, Belgium)
Trisodium citrate dihydrate (Jungbunzlauer, Switzerland)
Propylene glycol (BASF, Germany)
Glycerol (glycerine 4808, 99.5%, Oleon NV, Belgium).
Metabisulphite sodium (Merck, Germany)
Propyl gallate (Panreac Applichem, Germany)
Formulas 1-9.2 as given in table 1 are true solutions and were prepared as described below. A further formula 4.3 was prepared that differed from formula 4.2 only in the citric acid and sodium citrate content. sample 4.3 comprises 0.12 w/v % citric acid and 0.84 w/v % sodium citrate, whereas sample 4.2 has 0.20 and 0.60 w/v %, respectively. As a result, sample 4.3 has a pH of 6.5, whereas sample 4.2 has a pH of 5.5.

For a batch size of 100 ml, 0.026 g of colchicine is added to about 90 gr of purified water under light protected conditions (i.e. protected against artificial or sun light) at room temperature, and mixed until clear solution is obtained.

TABLE 1 composition of samples (w/v %)

| | | Sample | | | | | | | | | | |
|---|---|---|---|---|---|---|---|---|---|---|---|---|
| | | 1 gr | 2 gr | 3 gr | 4.1 gr | 4.2 gr | 5 gr | 6 gr | 7 gr | 8 gr | 9.1 gr | 9.2 gr |
| Colchicine (dry substance) | API | 0.025 | 0.025 | 0.025 | 0.025 | 0.025 | 0.025 | 0.025 | 0.025 | 0.025 | 0.012 | 0.012 |
| Hydroxyethylcellulose | Thickener | 0.2 | 0.2 | 0.2 | — | — | 0.2 | — | | | | |
| Xanthan gum | Thickener | | | | | | | | 0.15 | | | |

TABLE 1-continued composition of samples (w/v %)

| | | Sample | | | | | | | | | | |
|---|---|---|---|---|---|---|---|---|---|---|---|---|
| | | 1 gr | 2 gr | 3 gr | 4.1 gr | 4.2 gr | 5 gr | 6 gr | 7 gr | 8 gr | 9.1 gr | 9.2 gr |
| Methyl paraben | Antimicrobial | 0.18 | 0.18 | 0.18 | 0.18 | 0.2 | 0.18 | 0.18 | 0.18 | 0.18 | 0.18 | 0.2 |
| Propyl paraben | Antimicrobial | 0.018 | 0.018 | 0.018 | 0.018 | — | 0.018 | 0.018 | 0.018 | 0.018 | 0.018 | 0 |
| Sodium metabisulphite | Antioxidant | — | — | — | — | — | 0.8 | 0.8 | 0.8 | — | — | — |
| Propyl gallate | Antioxidant | — | — | — | — | — | — | — | — | 0.05 | — | — |
| Glycerol | Solvent | 5 | — | 2.5 | 10 | 10 | 5 | 10 | 5 | 10 | 10 | 10 |
| Propylene glycol | Solvent | — | 5 | 2.5 | — | — | — | — | — | — | — | — |
| Citric acid anhydrous | buffer | 0.2 | 0.2 | 0.2 | 0.2 | 0.2 | 0.2 | 0.2 | 0.2 | 0.2 | 0.2 | 0.2 |
| Na citrate 2H2O | buffer | 0.5 | 0.5 | 0.5 | 0.5 | 0.5 | 0.5 | 0.6 | 0.5 | 0.6 | 0.5 | 0.5 |
| Sucralose | sweetener | 0.135 | 0.135 | 0.135 | 0.135 | 0.135 | 0.135 | 0.135 | 0.135 | 0.135 | 0.135 | 0.135 |
| Orange flavour | flavour | 0.1 | 0.1 | 0.1 | 0.1 | 0.1 | 0.1 | 0.1 | 0.1 | 0.1 | 0.1 | 0.1 |
| Purified water | solvent | 93.6 | 93.6 | 93.6 | 88.8 | 88.8 | 92.8 | 87.9 | 92.9 | 88.7 | 88.8 | 88.8 |
| Total | | 100 | 100 | 100 | 100 | 100 | 100 | 100 | 100 | 100 | 100 | 100 |
| Final pH | | | | | | | 5.2-5.8 | | | | | |

0.2 g of sodium methyl paraben, or 0.18 g of sodium methyl paraben together with 0.018 g propyl paraben (depending of the formula), are added to the above aqueous mixture and mixed well until a clear solution is obtained.

0.12 to 0.2 g of citric acid anhydrous and 0.5 to 0.83 g of trisodium citrate dihydrate (depending of the formula) are added to the previous mixture and mixed well until clear solution.

0.135 g of sucralose is added and mixed well until clear solution.

If present, 0.8 g of sodium bisulphite or 0.05 g propyl gallate was added and mixed well until clear solution. In case of propyl gallate usage, mild heated should be applied up to 45° C., whereafter the solution is cooled to room temperature (22-25° C.).

Glycerol is added as follows: 2.5 g for a final concentration of 2.5 w/v %, 5 g for a final concentration of 5 w/v %, and 10 g for a final concentration of 10 w/v %. If present, 2.5 g of propylene glycol was add to provide a 2.5 w/v % solution, and 5 g for a 5 w/v % solution. Solvents are mixed well at room temperature with the rest until a clear solution is obtained.

If present, 0.15 g of xanthan gum or 0.2 g HEC was added and mixed, at room temperature, until complete dissolution. Depending the batch size this step could last up to 2 hours.

Flavour is added to the obtained solution in an amount of 0.1 w/v %, and purified water was added to a total volume of 100 ml.

The composition was filtered through a 10 μm sieve and filled in type III amber glass vials.

Analytical Procedures

Instrumentation:

Shimadzu (Duisburg, Germany) Prominence Series HPLC-DAD modular system consisting of: a DGU-20A5 mobile phase degasser, an LC-20 AD micro dual piston pump, an SIL-20ACHT autosampler, a CTO-20AC column oven, an SPD-M20 UV/Vis photodiode array detector, and a personal computer with Shimadzu LC Solutions software (v.1.11 SP1) installed for the system control, and the data record and process.

Reagents:

HPLC-grade water ($H_2O$) (resistivity>18 MΩ cm) by deionization and distillation;

Acetonitrile (ACN) (Fisher Chemical, Germany, HPLC grade);

Methanol (MeOH) (Fisher Chemical, HPLC grade)

Orthophosphoric acid (Fisher Chemical, Germany);

Potassium

Dihydrogen phosphate (LANH:NER)

Diluent

MeOH/$H_2O$: 50/50

Determination of Colchicine Content:

Column: ZORBAX Eclipse XDB C18, 250×4.6 mm, 5 μm, (Lot: B20441-P/N: 990967-902)

Reference: Colchicine Reference Standard, LGC, purity 93.0%, Lot. 1096857

Standard solution of colchicine (0.01 mg/ml): 10 mg Colchicine reference standard was transferred into a 10 ml volumetric flask. Diluent was added to adjust the volume to 10 ml, followed by vortex mixing for homogenizing. Of this solution, 0.1 ml was transferred into a 10 ml volumetric flask, diluted to the envisaged volume with diluent and vortexed/mixed to homogenize. Standard solutions were prepared in duplo.

Test solution (0.01 mg/ml): 0.2 ml sample oral solution was transferred into a 5.0 ml volumetric flask. Diluent was added followed by vortex mixing from homogenizing. Test solutions were prepared in duplo.

Chromatographic Parameters

Mobile Phase:

Dissolved 6.8 g/l of potassium dihydrogen phosphate: MeOH (45:55). The pH was adjusted to 5.5 with ortho-phosphoric acid. The buffer was subjected to filtration through a 0.45-μm membrane filter.

Injection Volume: 10 μl

Flow rate: 1.0 ml/min

Column temperature: 20° C.

Autosampler temperature: 25° C.

Run time: 23 minutes

Quantification wavelength: 350 nm

Procedures:

Six replicates of colchicine standard solution (before proceeding system suitability criteria should be met) and 2 replicates of verification standard solution were injected. The recovery against the mean areas of the two standard solutions were calculated. (The recovery should be between 98-102%). One replicate of each sample solution was injected.

System Suitability Criteria:
The 6 replicates of the standard solution were used:
a) % RSD≤2.0%
b) Tailing Factor≤1.5
c) Plate Count>2000

Calculation of the % Content of Colchicine by the Equation:

$$\% \text{ Colchicine} = \frac{Asmp * Vsmp * Wstd * Pstd * Dstd * 100}{Astd * Wsmp * LC * Dsmp * Vstd}$$

wherein: Asmp is the area of the colchicine peak in the chromatogram of the test solution; Astd is the area of the Colchicine peak in the chromatogram of the standard solution; LC is the Label Claim of the formulation (=0.25 mg/ml); Wstd is the accurate weigh of the Colchicine reference standard used for the preparation of the standard solution in mg; Vsmp is the initial volume of the colchicine sample solution in ml; Vstd is the initial volume of the colchicine standard solution in ml; Pstd is the purity of the standard in decimal form (% assay as is from CoA); Dstd is the dilution of the standard; and Dsmp is the dilution of the sample.

Determination of all Impurities (Except for Impurity A):
During manufacture and storage, impurities can be formed, mentioned in table 2 below.

Column: Agilent Extend C18 250×4 mm, 5 μm (Lot: B09110)

Reference solutions: Colchicine Reference Standard, LGC, purity 93.0%, Lot. 1096857, and Colchicine for system suitability CRS.

TABLE 2

| Ph. Eur. | USP | Product specs |
|---|---|---|
| Content 97.0%-102.0% (anhydrous substance<br>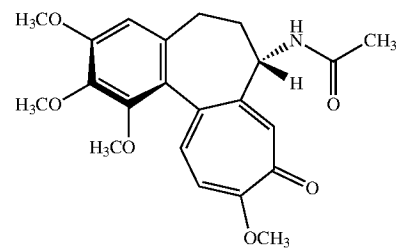<br>colchicine | Colchicine is an alkaloid contained in various species of Colchicum and in other genera. It contains NLT 94.0% and NMT 101.0% of colchicine (C22H25NO6), calculated on the anhydrous, solvent-free basis. | Reporting threshold: 0.1%<br>Identification threshold: 0.5%<br>Qualification threshold: 1.0% |
| Impurity A NMT 3.0%<br>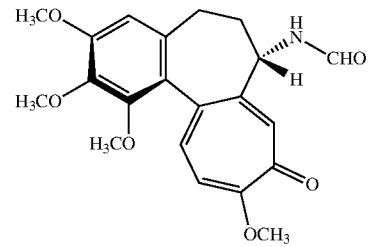<br>A. N-[(7S,12aM)-1,2,3,10-tetramethoxy-9-oxo-5,6,7,9-tetrahydrobenzo[a]heptalen-7-yl] formamide (N-deacetyl-N-fomylcolchicine) | Specified impurity<br>Indena:<br>Secondary plant metabolite and degradation product<br>Sary:<br>From starting material | NMT 3.0%<br>(acc. to ph. eur) |
| Impurity B<br>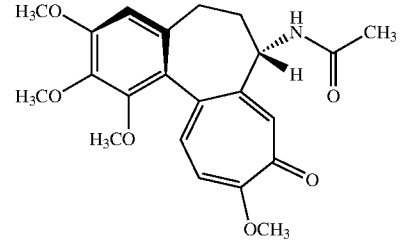<br>B. N-[(7S,12aP)-1,2,3,10-tetramethoxy-9-oxo-5,6,7,9-tetrahydrobenzo[a]heptalen-7-yl] acetamide (Conformational isomer) | Other detectable impurity<br>Conformational isomer of colchicine which is formed in situ in solution. Disregard peak due to impurity B<br>Indena: Not to be considered as impurity<br>Sary:<br>From starting material | NMT 1.0% |

TABLE 2-continued colchicine and impurities

| Ph. Eur. | USP | Product specs |
|---|---|---|
| Impurity C | Other detectable impurity Indena: Degradation product Sary: Photodegradant | NMT 1.0% Qualification threshold |

C. N-[(7S,7bR,10aS)-1,2,3,9-tetramethoxy-8-oxo-5,6,7,7b,8,10a-hexahydrobenzo[a]cyclopenta-[3,4]cyclobuta[1,2-c]cyclohepten-7-yl] acetamide (β-lumicolchicine)

| Ph. Eur. | USP | Product specs |
|---|---|---|
| Impurity D | Other detectable impurity Indena: Secondary plant metabolite Sary: Starting material isolation | NMT 0.5% (ICH Q3B R2, identification threshold) |

D. N-[(7S,12aM)-3-(β-D-glucopyranosyloxy)-1,2,10-trimethoxy-9-oxo-5,6,7,9-tetrahydro-benzo[a]heptalen-7-yl] acetamide (colchicoside)

| Ph. Eur. | USP | Product specs |
|---|---|---|
| Impurity E NMT 0.2% | Specified impurity Indena: Secondary plant metabolite Sary: From starting material | NMT 0.5% (ICH Q3B R2, identification threshold) |

E. N-[(7S,12aM)-3-hydroxy-1,2,10-trimethoxy-9-oxo-5,6,7,9-tetrahydrobenzo[a]heptalen-7-yl] acetamide (3-O-demethylcolchicine)

| Ph. Eur. | USP | Product specs |
|---|---|---|
| Impurity F NMT 0.2% - Cas no: 477-27-0 | Specified impurity Acceptance criteria: No definite green color is produced. Indena: Degradation product Sary: From starting material | NMT 1.0% Qualification threshold (from Indena) |

F. N-[(7S,12aM)-10-hydroxy-1,2,3-trimethoxy-9-

TABLE 2-continued colchicine and impurities

| Ph. Eur. | USP | Product specs |
|---|---|---|
| oxo-5,6,7,9-tetrahydrobenzo[a]heptalen-7-yl] acetamide (colchiceine) | | |
| Imp G NMT 0.25% 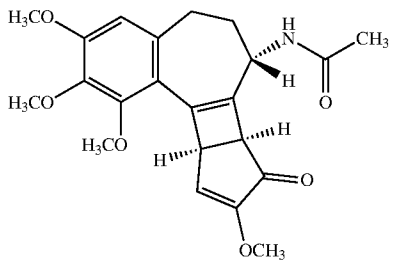 [SMILES: COC1=C[C@H]2C3=C([C@H]2C1=O)[C@@H](NC(C)=O)CCc1cc(OC)c(OC)c(OC)c13] G. N-[(7S,7bR,10aR)-1,2,3,9-tetramethoxy-8-oxo-5,6,7,7b,8,10a-hexahydrobenzo[a]cyclopenta-[3,4]cyclobuta[1,2-c]cyclohepten-7-yl] acetamide (γ-lumicolchicine) | Specified impurity Indena: Degradation product Sary: Photo degradant | NMT 1.0% Qualification threshold |
| Unspecified impurities_NMT 0.10% Total_NMT 4.0% | CHROMATOGRAPHIC PURITY Procedure: Proceed as directed in the Assay. Acceptance criteria: NMT 5.0% other than that due to colchicine, eluting within 1.5 times the retention time for colchicine | Unspecified impurities_NMT 0.5% (ICH Q3B R2, identification threshold) |

Reference Colchicine Solution (0.000125 mg/ml):

10 mg colchicine was transferred into a 10 ml volumetric flask. The envisaged volume was obtained by dilution with diluent followed by vortex mixing to homogenize. Of this solution, 0.1 ml was transferred into a 20 ml volumetric flask, diluted to volume with diluent and vortex mixed to homogenize.

Test solution (0.025 mg/ml): Of the sample preparation, 1.0 ml was transferred into a 10.0 ml volumetric flask. The envisaged volume was obtained by dilution with diluent followed by vortex mixing to homogenize. The obtained solution was filled in a HPLC vial.

System Suitability Solutions:

5 mg of Colchicine for system suitability CRS was transferred into a 5 ml volumetric flask and diluted to volume with diluent and vortex mixed to homogenize.

System Suitability Solution:

The 3 replicates of the standard solution for unknown impurities were used: % RSD≤2.0%, EP plate is NLT2000, Tailing factor is NMT 1.5. For the system suitability solution, the resolution between Impurity G and Impurity C should be >1.5.

Mobile phase A: 6.8 g of potassium dihydrogen phosphate was dissolved in 1000 ml HPLC water.

Mobile phase B: ACN: MeOH (60:40)

Mobile phase C: $H_2O$

Injection volume: 30 µl; autosampler temperature: 25° C.; flow rate 1 ml/min, column temperature 15° C.; run time: 50 minutes; quantification wavelength: 254 nm.

Gradient Program is shown in table 3.

TABLE 3

Gradient program

| Time (min) | Mobile phase A (% v/v) | Mobile phase B (% v/v) | Mobile phase C (% v/v) |
|---|---|---|---|
| 0-40 | 45 | 15 | 40 |
| 40-45 | 45 | 45 | 10 |
| 45.01 | 45 | 45 | 10 |
| 45.01-50 | 45 | 15 | 40 |

The colchicine content is calculated by the following equation:

$$\% \text{ Recovery} = \frac{Asmp \times Vsmp \times Wstd \times Pstd \times Dstd \times 100}{Astd \times LC \times Dsmp \times Vstd}$$

wherein: Asmp is the peak area response of colchicine in the sample solution chromatograms; Astd is the average peak area response of colchicine in the standard solution chromatograms; LC is the Label Claim of the formulation (=50 mg/2 ml); Wstd is the weight of the Colchicine standard in mg; Vsmp is the initial volume of the test solution in ml; Vstd is the initial volume of the standard solution in ml; Pstd is the purity of the standard in decimal form; Dstd is the standard dilution; and Dsmp is the sample dilution.

Under the chromatography conditions as described above, the relative retention time RRT for impurity B is 0.99, for impurity C: 1.26, for impurity E: 0.72, for impurity F: 1.16, and for impurity G, 1.26. The response factor RF is 0.91 for impurity G, and 1.30 for impurity C.

The product specification of a colchicine solution of formula 1 is depicted in table 4.

Determination of Impurity A
- Column: NUCLEOSIL EC 100-5 C8, 250×4 mm, 5 μm (Lot: 21000043-SN: E12060052)
- References: Colchicine Reference Standard, LGC, purity 93.0%, Lot. 1096857, and System Suitability for Impurity A, EP, CRS Y0001958, Batch 1.0.
- Reference colchicine solution (0.0005 mg/ml): 10 mg colchicine was transferred into a 10 ml volumetric flask. The envisaged volume was obtained by dilution with diluent followed by vortex mixing to homogenize. Of this solution, 0.05 ml was transferred into a 10 ml volumetric flask, diluted to volume with diluent and vortex mixed to homogenize. 0.1 ml of this solution was transferred to the HPLC vial, 0.9 ml diluent was added and vortex mixed to homogenize.
- Test solution (0.1 mg/ml): Of the sample preparation, 2.0 ml was transferred into a 5.0 ml volumetric flask. The envisaged volume was obtained by dilution with diluent followed by vortex mixing to homogenize. The obtained solution was filled in a HPLC vial.
- System Suitability solutions: 10 mg of Impurity A was diluted with diluent to volume in a 10 ml volumetric flask and vortex mixed to homogenize (Impurity A stock solution). 10 mg of colchicine was diluted with diluent in a 10 ml volumetric flask and vortex mixed to homogenize (Colchicine stock solution). 0.03 ml of Impurity A stock solution and 1 ml of Colchicine stock solution were diluted to volume with diluent in a 10 ml volumetric flask, and vortex mixed to homogenize.
- System suitability solution: The 3 replicates of the standard solution for unknown impurities were used: % RSD≤2.0%, EP plate is NLT2000, Tailing factor is NMT 1.5. For the system suitability solution, the resolution between Impurity A and colchicine should be >1.5.
- Mobile phase: 6.8 g of potassium dihydrogen phosphate was dissolved in 1000 ml HPLC water:MeOH (45:55), and the pH was adjusted to 5.5 with orthophosphoric acid. The solution was subjected to filtration through a 0.45 μm membrane.
- Injection volume: 10 μl; autosampler temperature: 25° C.; flow rate 1 ml/min, column temperature 25° C.; run time: 23 minutes; quantification wavelength: 254 nm.

The percentage of colchicine content was calculated with the same equation as presented in the previous section for all impurities.

Under the chromatography conditions as described above, the relative retention time RRT for impurity A is 0.9, and the response factor RF is 0.84.

TABLE 4

Product specification Solution Formula 1 after production

| | TESTS | METHOD | SPECIFICATIONS | |
|---|---|---|---|---|
| 1 | Appearance | Visual inspection | Amber glass bottle with cap | |
| 2 | Clarity and degree of opalescence of liquids | Ph. Eur. cur. ed. (2.2.1) | Clear solution | |
| 3 | Degree of coloration of the liquids | Ph. Eur. cur. ed. (2.2.2) | Clear solution | |
| 4 | pH | Ph. Eur. cur. ed. (2.2.3) | 5.6-5.9 | |
| 5 | Relative Density | Ph. Eur. cur. ed. (2.2.5) | 1.00-1.05 | |
| 6 | Uniformity of mass of delivered doses | Ph. Eur. cur. ed. (2.9.27) | Meets the requirements | |
| 7 | Uniformity of dosage units | Ph. Eur. cur. ed. (2.9.40) | Meets the requirements (MV) | |
| 8 | Deliverable Volume | USP <698> | Meets the requirements | |
| 9 | Package integrity | In house method | Pass | |
| 10 | Identification Colchicine | HPLC (UV) HPLC (Diode Array) | Retention time complies with RS UV spectrum complies with RS | |
| 11 | Identification methylparaben | HPLC (UV) | Retention time complies with RS | |
| 14 | Assay of colchicine | In - house method Ph. Eur. cur. ed. (2.2.29) | 95.0-105.0% of the stated amount of colchicine | |
| 15 | Assay of methylparaben | In house method Ph. Eur. cur. ed. (2.2.29) | Each 90.0-110.0% | |
| 18 | Related Substances | In house method Ph. Eur. cur. ed. (2.2.29) | imp A | NMT 3.0% |
| | | | imp B | NMT 1.0% |
| | | | imp C | NMT 1.0% |
| | | | imp D | NMT 0.5% |
| | | | imp E | NMT 0.5% |
| | | | imp F | NMT 0.5% |
| | | | imp G | NMT 1.0% |
| | | | Any unspecified impurity | NMT 0.5% |
| | | | Total Impurities | NMT 5.0% |
| 19 | Microbial Limits Testing | | | |
| | Total Aerobic Microbial Count | Ph. Eur. cur. ed. (5.1.4) | 100 CFU/mL | |
| | Total Combined Yeasts/Moulds | | 10 CFU/mL | |
| | E. Coli | | Absent/1 mL | |
| 20 | Antimicrobial Effectiveness Testing | Ph. Eur. cur. ed. (5.1.3) | Pass | |

Stability

Stability tests of samples 1-9.2 of table 1 are depicted in tables 5-18 and are discussed below. The samples were all placed in ICH stability chambers. The humidity was 60% in the tests at 5° C. and 25° C., 65% in the tests at 30° C. and 75% at the tests at 40° C. GLP are Glopebra samples.

TABLE 5 stability test
time zero

| | 1 | 2 | 3 | 4.1 | 4.2 | 5 | 6 | 7 | 8 | 9.1 | 9.2 | GLP |
|---|---|---|---|---|---|---|---|---|---|---|---|---|
| assay colchicine | 101.10 | 100.20 | 101.20 | 101.00 | 101.30 | 97.50 | 99.50 | 98.30 | 101.40 | 101.00 | 98.80 | 105.60 |
| imp A | 0.40 | 0.41 | 0.36 | 0.30 | 0.31 | 0.45 | 0.41 | 0.35 | 0.44 | 0.35 | 0.33 | 0.48 |
| imp B | 0.20 | 0.22 | 0.24 | 0.27 | 0.26 | 0.22 | 0.24 | | 0.12 | 0.10 | 0.06 | 0.42 |
| imp C | | | | | | | | | | | | |
| imp D | | | | | | 0.11 | 0.13 | | | | | |
| imp E | | | | 0.10 | 0.10 | | | | | | | |
| imp F | | | | | | | | | | | | |
| imp G | | | | | | | | | | | | |
| Unspec. Imp | | | | | | 1.02 | 0.72 | | | | | 0.41 |
| Total Impurities | 0.60 | 0.63 | 0.60 | 0.67 | 0.67 | 0.78 | 1.80 | 1.07 | 0.56 | 0.45 | 0.39 | 1.31 |

TABLE 6

Stability test
2 months at 25° C.

| | 1 | 2 | 3 | 4.1 | 4.2 | 5 | 6 | 7 | 8 | 9.1 | 9.2 |
|---|---|---|---|---|---|---|---|---|---|---|---|
| assay colchicine | 101.00 | 99.80 | 101.00 | 100.80 | 100.80 | 96.10 | 99.00 | 97.50 | 101.00 | 101.00 | 98.80 |
| imp A | 0.41 | 0.43 | 0.44 | 0.30 | 0.32 | 0.50 | 0.40 | 0.41 | 0.46 | 0.35 | 0.35 |
| imp B | 0.42 | 0.48 | 0.44 | 0.45 | 0.45 | 0.43 | 0.46 | 0.43 | 0.38 | 0.15 | 0.12 |
| imp C | | | | | | | | | | | |
| imp D | | | | | | | | | | | |
| imp E | | | | | | | | | | | |
| imp F | | | | | | | | | | | |
| imp G | | 0.10 | 0.10 | | | | | | | | |
| Unspec. Imp | | | | | | 1.16 | 0.65 | 0.91 | | | |
| Total Impurities | 0.83 | 1.01 | 0.98 | 0.75 | 0.77 | 2.09 | 1.51 | 1.75 | 0.84 | 0.50 | 0.47 |

TABLE 7

Stability test
5 months at 25° C.

| | 1 | 2 | 3 | 4.1 | 4.2 | 5 | 6 | 7 | 8 | 9.1 | 9.2 | GLP |
|---|---|---|---|---|---|---|---|---|---|---|---|---|
| assay colchicine | 100.80 | 99.80 | 100.20 | 100.00 | 100.00 | 95.50 | 99.10 | 96.00 | 101.00 | 100.80 | 98.50 | 105.30 |
| imp A | 0.42 | 0.48 | 0.48 | 0.30 | 0.38 | 0.52 | 0.54 | 0.47 | 0.50 | 0.36 | 0.37 | 0.57 |
| imp B | 0.48 | 0.57 | 0.50 | 0.51 | 0.49 | 0.49 | 0.59 | 0.48 | 0.45 | 0.17 | 0.15 | 0.57 |
| imp C | | | | | | | | | | | | |
| imp D | | | | | | | | | | | | |
| imp E | | | | | | | | | | | | |
| imp F | | 0.10 | 0.10 | | | | 0.11 | | | | | |
| imp G | 0.11 | 0.10 | 0.10 | 0.10 | 0.11 | | | | | | | |
| Unspec. Imp | | | | | | 1.25 | 0.87 | 1.12 | | | | 0.44 |
| Total Impurities | 1.01 | 1.25 | 1.18 | 0.91 | 0.98 | 2.26 | 2.11 | 2.07 | 0.95 | 0.53 | 0.52 | 1.58 |

TABLE 8

Stability test
6 months at 25° C.

| | 1 | 2 | 3 | 4.1 | 4.2 | 5 6 7 | 8 | 9.1 | 9.2 |
|---|---|---|---|---|---|---|---|---|---|
| assay colchicine | 100.50 | 99.50 | 100.00 | 99.50 | 99.60 | | 100.20 | 100.10 | 98.40 |
| imp A | 0.51 | 0.5 | 0.35 | 0.30 | 0.34 | | 0.37 | 0.36 | 0.38 |
| imp B | 0.57 | 0.60 | 0.58 | 0.52 | 0.54 | | 0.41 | 0.25 | 0.22 |
| imp C | | | | | | | | | |
| imp D | | | | | | | | | |

TABLE 8-continued

Stability test
6 months at 25° C.

| | 1 | 2 | 3 | 4.1 | 4.2 | 5 6 7 | 8 | 9.1 | 9.2 |
|---|---|---|---|---|---|---|---|---|---|
| imp E | | | | | | | | | |
| imp F | | | 0.12 | | | | | | |
| imp G | 0.10 | 0.10 | 0.10 | 0.13 | 0.12 | | | | |
| Unspec. Imp | | | | | | | | | |
| Total Impurities | 1.18 | 1.20 | 1.15 | 0.95 | 1.00 | | 0.78 | 0.61 | 0.60 |

TABLE 9

Stability test
2 months at 30° C.

| | 1 | 2 | 3 | 4.1 | 4.2 | 5 | 6 | 7 | 8 | 9.1 | 9.2 |
|---|---|---|---|---|---|---|---|---|---|---|---|
| assay colchicine | 101.00 | 99.70 | 100.50 | 100.60 | 100.00 | 95.10 | 98.80 | 97.50 | 100.90 | 100.90 | 98.70 |
| imp A | 0.45 | 0.50 | 0.49 | 0.31 | 0.32 | 0.50 | 0.54 | 0.47 | 0.53 | 0.35 | 0.35 |
| imp B | 0.42 | 0.55 | 0.44 | 0.45 | 0.46 | 0.43 | 0.46 | 0.43 | 0.38 | 0.18 | 0.16 |
| imp C | | | | | | | | | | | |
| imp D | | | | | | | | | | | |
| imp E | | | | | | | | | | | |
| imp F | | | | | | | | | | | |
| imp G | | 0.10 | 0.10 | | | | | | | | |
| Unspecified impurities | | | | | | 1.16 | 0.65 | 0.91 | | | |
| Total Impurities | 0.87 | 1.15 | 1.03 | 0.76 | 0.78 | 2.09 | 1.65 | 1.81 | 0.91 | 0.53 | 0.51 |

TABLE 10

Stability test
5 months at 30° C.

| | 1 | 2 | 3 | 4.1 | 4.2 | 5 | 6 | 7 | 8 | 9.1 | 9.2 | GLP |
|---|---|---|---|---|---|---|---|---|---|---|---|---|
| assay colchicine | 100.10 | 99.60 | 99.80 | 100.20 | 99.50 | 94.80 | 97.80 | 97.00 | 100.80 | 100.80 | 98.50 | 105.70 |
| imp A | 0.47 | 0.50 | 0.50 | 0.32 | 0.38 | 0.53 | 0.55 | 0.43 | 0.52 | 0.36 | 0.37 | 0.60 |
| imp B | 0.50 | 0.57 | 0.56 | 0.51 | 0.48 | 0.49 | 0.6 | 0.49 | 0.46 | 0.34 | 0.32 | 0.50 |
| imp C | | | | | | | | | | | | |
| imp D | | | | | | | | | | | | |
| imp E | | | | | | | | | | | | |
| imp F | | | | | | | 0.10 | 0.12 | | | | |
| imp G | 0.10 | 0.10 | 0.12 | 0.11 | 0.10 | | | | | | | |
| Unspec. Imp | | | | | | 1.32 | 0.93 | 1.46 | | | | 0.44 |
| Total Impurities | 1.07 | 1.17 | 1.18 | 0.94 | 0.96 | 2.34 | 2.18 | 2.50 | 0.98 | 0.70 | 0.69 | 1.54 |

TABLE 11

Stability test
6 months at 30° C.

| | 1 | 2 | 3 | 4.1 | 4.2 | 5 | 6 | 7 | 8 | 9.1 | 9.2 |
|---|---|---|---|---|---|---|---|---|---|---|---|
| assay colchicine | 99.60 | 99.00 | 99.60 | 99.70 | 99.20 | | | | 101.00 | 99.30 | 98.10 |
| imp A | 0.52 | 0.52 | 0.50 | 0.34 | 0.38 | | | | 0.36 | 0.35 | 0.34 |
| imp B | 0.57 | 0.60 | 0.60 | 0.47 | 0.49 | | | | 0.56 | 0.37 | 0.35 |
| imp C | | | | | | | | | | | |
| imp D | | | | | | | | | | | |
| imp E | | | | | | | | | | | |
| imp F | 0.10 | | | | | | | | | | |
| imp G | 0.12 | 0.10 | 0.13 | 0.12 | 0.11 | | | | | | |
| Unspec. Imp | | | | | | | | | | | |
| Total Impurities | 1.31 | 1.22 | 1.23 | 0.93 | 0.98 | | | | 0.92 | 0.72 | 0.69 |

TABLE 12

Stability test
2 months at 40° C.

| | 1 | 2 | 3 | 4.1 | 4.2 | 5 | 6 | 7 | 8 | 9.1 | 9.2 |
|---|---|---|---|---|---|---|---|---|---|---|---|
| assay colchicine | 100.80 | 99.70 | 99.80 | 100.40 | 99.50 | 94.80 | 98.10 | 97.40 | 100.70 | 100.80 | 98.60 |
| imp A | 0.46 | 0.50 | 0.51 | 0.30 | 0.31 | 0.50 | 0.54 | 0.47 | 0.52 | 0.45 | 0.44 |
| imp B | 0.44 | 0.55 | 0.47 | 0.45 | 0.52 | 0.43 | 0.46 | 0.43 | 0.38 | 0.19 | 0.18 |
| imp C | | | | | | | | | | | |
| imp D | | | | | | | | | | | |
| imp E | | | | | | | | | | | |
| imp F | | | | | | | | | | | |
| imp G | | 0.10 | 0.10 | | | | | | | | |
| Unspec. Imp | | | | | | 1.16 | 0.65 | 0.91 | | | |
| Total Impurities | 0.90 | 1.15 | 1.08 | 0.75 | 0.83 | 2.09 | 1.65 | 1.81 | 0.90 | 0.64 | 0.62 |

TABLE 13

Stability test
5 months at 40° C.

| | 1 | 2 | 3 | 4.1 | 4.2 | 5 | 6 | 7 | 8 | 9.1 | 9.2 | GLP |
|---|---|---|---|---|---|---|---|---|---|---|---|---|
| assay colchicine | 99.80 | 99.50 | 99.00 | 99.80 | 99.20 | 94.10 | 97.50 | 96.80 | 97.50 | 100.50 | 98.50 | 104.40 |
| imp A | 0.52 | 0.50 | 0.50 | 0.34 | 0.32 | 0.43 | 0.44 | 0.40 | 0.46 | 0.45 | 0.46 | 0.58 |
| imp B | 0.51 | 0.60 | 0.60 | 0.56 | 0.60 | 0.44 | 0.57 | 0.51 | 1.09 | 0.25 | 0.26 | 0.53 |
| imp C | | | | | | | | | 0.12 | | | |
| imp D | | | | | | | | | | | | |
| imp E | | | | | 0.12 | | | | | | | |
| imp F | | | | | | | | | | | | |
| imp G | 0.12 | 0.15 | 0.16 | 0.12 | | | | | | | | |
| Unspec. Imp | 0.00 | | | | | 2.14 | 1.85 | 1.88 | 3.20 | | | 0.55 |
| Total Impurities | 1.15 | 1.25 | 1.26 | 1.02 | 1.04 | 3.01 | 2.86 | 2.79 | 4.87 | 0.70 | 0.72 | 1.66 |

TABLE 14

Stability test
6 months at 40° C.

| | 1 | 2 | 3 | 4.1 | 4.2 | 5 | 6 | 7 | 8 | 9.1 | 9.2 |
|---|---|---|---|---|---|---|---|---|---|---|---|
| assay colchicine | 99.60 | 99.00 | 98.70 | 99.50 | 99.00 | | | | 98.00 | 100.10 | 98.00 |
| imp A | 0.53 | 0.55 | 0.51 | 0.37 | 0.39 | | | | 0.36 | 0.39 | 0.41 |
| imp B | 0.58 | 0.62 | 0.68 | 0.63 | 0.71 | | | | 0.94 | 0.37 | 0.37 |
| imp C | | | | | | | | | 0.10 | | |
| imp D | | | | | | | | | | | |
| imp E | | | | | | | | | | | |
| imp F | 0.12 | 0.11 | 0.16 | 0.11 | | | | | | 0.10 | |
| limp G | 0.11 | 0.12 | 0.10 | 0.11 | 0.10 | | | | 0.15 | | |
| Unspec. Imp | | | | | | | | | 3.25 | | |
| Total Impurities | 1.34 | 1.40 | 1.45 | 1.22 | 1.20 | | | | 4.80 | 0.86 | 0.78 |

TABLE 15

Stability test
2 months at 5° C.

| | 1 | 2 | 3 | 4.1 | 4.2 | 5 | 6 | 7 | 8 | 9.1 | 9.2 |
|---|---|---|---|---|---|---|---|---|---|---|---|
| assay colchicine | 101.00 | 99.70 | 100.50 | 100.70 | 100.60 | 95.40 | 98.10 | 96.40 | 100.90 | 100.80 | 98.40 |
| imp A | 0.45 | 0.50 | 0.51 | 0.30 | 0.30 | 0.50 | 0.54 | 0.47 | 0.52 | 0.38 | 0.33 |
| imp B | 0.42 | 0.48 | 0.44 | 0.45 | 0.48 | 0.43 | 0.46 | 0.43 | 0.38 | 0.11 | 0.10 |
| imp C | | | | | | | | | | | |
| imp D | | | | | | | | | | | |
| imp E | | | | | | | | | | | |

TABLE 15-continued

Stability test
2 months at 5° C.

|  | 1 | 2 | 3 | 4.1 | 4.2 | 5 | 6 | 7 | 8 | 9.1 | 9.2 |
|---|---|---|---|---|---|---|---|---|---|---|---|
| imp F |  |  |  |  |  |  |  |  |  |  |  |
| impG |  | 0.10 | 0.10 |  |  |  |  |  |  |  |  |
| Unspec. Imp |  |  |  |  |  | 1.16 | 0.65 | 0.91 |  |  |  |
| Total Impurities | 0.87 | 1.08 | 1.05 | 0.75 | 0.78 | 2.09 | 1.65 | 1.81 | 0.90 | 0.49 | 0.43 |

TABLE 16

Stability test
5 months at 5° C.

|  | 1 | 2 | 3 | 4.1 | 4.2 | 5 | 6 | 7 | 8 | 9.1 | 9.2 | GLP |
|---|---|---|---|---|---|---|---|---|---|---|---|---|
| assay colchicine | 100.50 | 98.70 | 100.20 | 100.40 | 99.80 | 95.20 | 97.80 | 96.80 | 100.80 | 100.70 | 98.70 | 105.70 |
| imp A | 0.48 | 0.49 | 0.54 | 0.32 | 0.32 | 0.48 | 0.48 | 0.49 | 0.51 | 0.38 | 0.35 | 0.53 |
| imp B | 0.50 | 0.60 | 0.56 | 0.47 | 0.50 | 0.48 | 0.60 | 0.49 | 0.49 | 0.12 | 0.11 | 0.50 |
| imp C |  |  |  |  |  |  |  |  |  |  |  |  |
| imp D |  |  |  |  |  |  |  |  |  |  |  |  |
| imp E |  |  |  |  |  |  |  |  |  |  |  |  |
| imp F |  |  |  |  |  |  |  |  |  |  |  |  |
| imp G | 0.11 | 0.10 | 0.10 | 0.00 |  |  |  |  |  |  |  |  |
| Unspec. Imp |  |  |  |  |  | 1.69 | 0.66 | 0.78 |  |  |  | 0.41 |
| Total Impurities | 1.09 | 1.19 | 1.20 | 0.79 | 0.82 | 2.65 | 1.74 | 1.76 | 1.00 | 0.50 | 0.46 | 1.44 |

TABLE 17

Stability test
6 months at 5° C.

|  | 1 | 2 | 3 | 4.1 | 4.2 | 5 | 6 | 7 | 8 | 9.1 | 9.2 |
|---|---|---|---|---|---|---|---|---|---|---|---|
| assay colchicine | 100.20 | 98.20 | 100.00 | 100.00 | 99.50 |  |  |  | 100.40 | 100.20 | 98.50 |
| imp A | 0.50 | 0.5 | 0.36 | 0.35 | 0.34 |  |  |  | 0.34 | 0.29 | 0.28 |
| imp B | 0.53 | 0.61 | 0.56 | 0.55 | 0.57 |  |  |  | 0.4 | 0.19 | 0.59 |
| imp C |  |  |  |  |  |  |  |  |  |  |  |
| imp D |  |  |  |  |  |  |  |  |  |  |  |
| imp E |  |  |  |  |  |  |  |  |  |  |  |
| imp F |  | 0.10 |  | 0.10 | 0.10 |  |  |  |  |  |  |
| imp G | 0.10 | 0.11 | 0.10 |  |  |  |  |  |  |  |  |
| Unspec. Imp |  |  |  |  |  |  |  |  |  |  |  |
| Total Impurities | 1.13 | 1.32 | 1.02 | 1.00 | 1.01 |  |  |  | 0.74 | 0.48 | 0.87 |

TABLE 18

Stability test
stress studies

|  | 1 (pH 8.5) | 4.1 light stress | 6 (pH 3.5) |
|---|---|---|---|
| assay colchicine | 99.10 | 74.20 | 100.50 |
| imp A | 0.40 | 0.08 | 0.40 |
| imp B | 0.20 | 0.15 | 0.29 |
| imp C |  | 26.26 |  |
| imp D |  |  |  |
| imp E |  |  | 0.10 |
| imp F |  | 2.36 |  |
| imp G |  |  |  |
| Unspec. Imp | 5.98 |  | 0.58 |
| Total Impurities | 6.60 | 28.85 | 1.37 |

From the stability data, it can clearly be observed that samples 4.1 and 4.2 as well as samples 9 and 9.1, all without thickener and without antioxidant have the overall highest stability as can be seen by the percentage of the impurities as compared to the same sample at time zero (lowest row in tables 3-9). The stability is better than from the known product Glopebra. The solution comprising the antioxidant propyl gallate (sample 8) is stable at 5° C., content of 2.5% seem to have slightly less long term stability as compared to the formulas with a lower colchicine content of 1.25%.

Solutions that comprise glycerol as sole water miscible solvent (samples 1, 4 and 9) have a higher stability than a mixture of 50:50 (on weight basis) glycerol and propylene glycol (sample 3). Also, sample 1 seems to be more stable than solutions that have propylene glycol as sole water miscible solvent.

The low stability of sample 5 indicates that the combination of thickener and sodium metabisulphite as antioxidant do not seem to be compatible.

From the stress data in table 18 it can be seen that a basic pH, but in particular light results in severe loss of stability. A low pH of 3.5 does not seem to have a significant impact on the stability.

Microbial Efficacy

Formulas 4.2 and 4.3 were tested for efficacy of antimicrobial preservation according to the teaching of the European Pharmacopeia 9.0, section 5.1.3, pp 577 ff. by Quality Assurance & Control Systems Ltd., Athens, Greece. Further, two formulas as formula 4.2, wherein only 70% of the paraben (i.e. 0.14 w/v %) or no paraben was present were tested as well. The test consists of challenging the sample solution with a prescribed inoculum of suitable micro-organisms as shown in the tables 19A-D, storing the inoculated solution at ambient temperature, avoiding sunlight, withdrawing samples from the container at specified intervals of time and counting the micro-organisms in the samples so removed. The preservative properties of the solution are adequate if, in the conditions of the test, there is a significant fall or no increase, as appropriate, in the number of micro-organisms in the inoculated solution after 14 and 28 days. ATCC stands for the deposit number of the micro-organism at the American Type Culture Collection ATCC.

TABLE 19A

Presevation efficacy sample 4.2 - no paraben

| Micro-organism | ATCC | Lot | Inoculation Cfu/g | Time zero | Day 14 | Day 28 |
|---|---|---|---|---|---|---|
| Pseudomonas aeruginosa | 9027 | 48412452 | $7.0 \times 10^5$ | $6.3 \times 10^5$ | <10 | <10 |
| Staphylococcus aureus | 6538 | 4854821 | $5.3 \times 10^5$ | $6.0 \times 10^5$ | <10 | <10 |
| Escherichia coli | 8739 | 4835664 | $8.7 \times 10^5$ | $7.9 \times 10^5$ | $2.5 \times 10^5$ | $5.2 \times 10^4$ |
| Candida albicans | 10231 | 4435903 | $3.8 \times 10^5$ | $3.3 \times 10^5$ | $2.9 \times 10^5$ | $3.3 \times 10^6$ |
| Aspergillus brasiliensis | 16404 | 3929552 | $2.0 \times 10^5$ | $8.8 \times 10^4$ | $2.0 \times 10^5$ | $1.7 \times 10^5$ |

TABLE 19B

Presevation efficacy sample 4.2 - 0.14 w/v % methylparaben

| Micro-organism | ATCC | Lot | Inoculation Cfu/g | Time zero | Day 14 | Day 28 |
|---|---|---|---|---|---|---|
| Pseudomonas aeruginosa | 9027 | 48412452 | $7.1 \times 10^5$ | $7.1 \times 10^5$ | <10 | <10 |
| Staphylococcus aureus | 6538 | 4854821 | $5.3 \times 10^5$ | $6.5 \times 10^5$ | <10 | <10 |
| Escherichia coli | 8739 | 4835664 | $8.7 \times 10^5$ | $8.4 \times 10^5$ | <10 | <10 |
| Candida albicans | 10231 | 4435903 | $3.8 \times 10^5$ | $3.5 \times 10^5$ | <‖10 | <10 |
| Aspergillus brasiliensis | 16404 | 3929552 | $2.0 \times 10^5$ | $1.5 \times 10^5$ | $2.4 \times 10^3$ | $1.2 \times 10^2$ |

TABLE 19C

Presevation efficacy sample 4.2 - 0.2 w/v % methylparaben

| Micro-organism | ATCC | Lot | Inoculation Cfu/g | Time zero | Day 14 | Day 28 |
|---|---|---|---|---|---|---|
| Pseudomonas aeruginosa | 9027 | 48412452 | $7.0 \times 10^5$ | $7.3 \times 10^5$ | <10 | <10 |
| Staphylococcus aureus | 6538 | 4854821 | $5.3 \times 10^5$ | $5.3 \times 10^5$ | <10 | <10 |
| Escherichia coli | 8739 | 4835664 | $8.7 \times 10^5$ | $8.4 \times 10^5$ | <10 | <10 |
| Candida albicans | 10231 | 4435903 | $3.8 \times 10^5$ | $4.4 \times 10^5$ | <10 | <10 |
| Aspergillus brasiliensis | 16404 | 3929552 | $2.0 \times 10^5$ | $2.8 \times 10^5$ | <10 | <10 |

TABLE 19D

Presevation eff. sample 4.1 - 0.126 w/v % methylparaben, 0.013 w/v % propylparaben

| Micro-organism | ATCC | Lot | Inoculation Cfu/g | Time zero | Day 14 | Day 28 |
|---|---|---|---|---|---|---|
| Pseudomonas aeruginosa | 9027 | 48412452 | $8.9 \times 10^5$ | $1.5 \times 10^4$ | <10 | <10 |
| Staphylococcus aureus | 6538 | 4854821 | $7.2 \times 10^5$ | $7.2 \times 10^5$ | <10 | <10 |
| Escherichia coli | 8739 | 4835664 | $9.7 \times 10^5$ | $8.0 \times 10^5$ | <10 | <10 |
| Candida albicans | 10231 | 4435903 | $4.9 \times 10^5$ | $5.5 \times 10^5$ | <10 | <10 |
| Aspergillus brasiliensis | 16404 | 3929552 | $2.5 \times 10^5$ | $1.1 \times 10^5$ | $2.2 \times 10^3$ | $7.6 \times 10^2$ |

TABLE 19E

Presevation efficacy sample 4.1 - 0.18 w/v % methylparaben, 0.018 w/v % propylparaben

| Micro-organism | ATCC | Lot | Inoculation Cfu/g | Time zero | Day 14 | Day 28 |
|---|---|---|---|---|---|---|
| Pseudomonas aeruginosa | 9027 | 48412452 | $7.0 \times 10^5$ | $6.3 \times 10^5$ | <10 | <10 |
| Staphylococcus aureus | 6538 | 4854821 | $5.3 \times 10^5$ | $6.7 \times 10^5$ | <10 | <10 |
| Escherichia coli | 8739 | 4835664 | $8.7 \times 10^5$ | $8.8 \times 10^5$ | <10 | <10 |
| Candida albicans | 10231 | 4435903 | $3.8 \times 10^5$ | $4.0 \times 10^5$ | <10 | <10 |
| Aspergillus brasiliensis | 16404 | 3929552 | $2.0 \times 10^5$ | $1.4 \times 10^5$ | $5.5 \times 10^1$ | <10 |

TABLE 19F

Presevation efficacy sample 4.3 - 0.2 w/v % methylparaben

| Micro-organism | ATCC | Lot | Inoculation Cfu/g | Time zero | Day 14 | Day 28 |
|---|---|---|---|---|---|---|
| Pseudomonas aeruginosa | 9027 | 48412452 | $7.0 \times 10^5$ | $7.5 \times 10^5$ | <10 | <10 |
| Staphylococcus aureus | 6538 | 4854821 | $5.3 \times 10^5$ | $6.9 \times 10^5$ | <10 | <10 |
| Escherichia coli | 8739 | 4835664 | $8.7 \times 10^5$ | $8.4 \times 10^5$ | <10 | <10 |
| Candida albicans | 10231 | 4435903 | $3.8 \times 10^5$ | $4.5 \times 10^5$ | $1.8 \times 10^1$ | $1.8 \times 10^1$ |
| Aspergillus brasiliensis | 16404 | 3929552 | $2.0 \times 10^5$ | $2.1 \times 10^5$ | $6.4 \times 10^1$ | <10 |

From the stability tests it can be observed that formula 4.2, having a pH of 5.5, appeared to be more stable than formula 4.3, having a pH of 6.5. Further, without paraben, the microbial efficacy was below acceptable level. Similar results were obtained when instead of methylparaben, a combination of methylparaben and propylparaben in a weight ratio of 10:1 was used (formula 4.1).

The invention claimed is:

1. A buffered aqueous colchicine solution or suspension being free of benzyl alcohol, propylene glycol and thickener, comprising colchicine, a water miscible solvent and a preservative, wherein the solution or suspension comprises 0.02-1.0 w/v % colchicine, 2.5-15.0 w/v % glycerol and 0.05-1 w/v % preservative, the pH of the solution or suspension being 3.5-7.0.

2. Buffered aqueous colchicine solution or suspension of claim 1, comprising 0.022-0.035 w/v % colchicine.

3. Buffered aqueous colchicine solution or suspension of claim 1, comprising 5-12 w/v % glycerol.

4. Buffered aqueous colchicine solution or suspension of claim 1, comprising 0.10-0.40 w/v % preservative.

5. Buffered aqueous colchicine solution or suspension of claim 1, wherein the preservative is chosen from the group, consisting of methyl paraben, ethyl paraben, propyl paraben, butyl paraben, sorbic acid, potassium sorbate, and combinations thereof.

6. Buffered aqueous colchicine solution or suspension of claim 1, having a pH of 4.5-6.5.

7. Buffered aqueous colchicine solution or suspension of claim 1, comprising 0.05-2.0 w/v % buffering agent.

8. Buffered aqueous colchicine solution or suspension of claim 1, comprising a buffering agent chosen from the group consisting of hydrochloric acid, acetic acid, ammonia solutions, monoethanolamine, diethanolamine, triethanolamine, meglumine, sodium citrate, citric acid, lactic acid, phosphoric acid, propionic acid, sulphuric acid, tartaric acid, potassium bicarbonate, potassium citrate, potassium hydroxide, sodium bicarbonate, sodium borate, and sodium hydroxide.

9. Buffered aqueous colchicine solution or suspension of claim 1, comprising 1.0 w/v % or less antioxidant.

10. Buffered aqueous colchicine solution or suspension of claim 9, wherein the antioxidant is chosen from the group, consisting of butylated hydroxyl anisole, butylated hydroxyl toluene, tocopherol, ascorbyl palmitate, ascorbic acid, sodium metabisulfite, sodium sulphite, sodium thiosulfate, propyl gallate, and combinations thereof.

11. Buffered aqueous colchicine solution or suspension of claim 1, being free of antioxidant.

12. Buffered aqueous colchicine solution or suspension of claim 1, comprising a sweetening agent, wherein the amount of sweetening agent in the solution or suspension has a sweetening power that corresponds with the sweetening power of 20-500 w/v % saccharose.

13. Buffered aqueous colchicine solution or suspension of claim 12, wherein the sweetening agent is an artificial sweetening agent, chosen from the group consisting of sucralose, sodium saccharin, aspartame, alitame, acesulfame-K, cyclamate, stevioside, glycyrrhizin, neohesperidin, dihydrochalcone, thaumatin, and combinations thereof.

14. Buffered aqueous colchicine solution or suspension of claim 1, comprising 0.05-0.3 w/v % sweetener.

15. Buffered aqueous colchicine solution or suspension of claim 1, comprising, in addition to glycerol, a water-miscible organic solvent selected from the group consisting of polyols, alcohols, acetone, phthalates, dimethyl sulfoxide, dimethylacetamide, glycofurol, isopropyl myristate, isopropyl palmitate, propylene carbonate, pyrrolidine, glycerine triacetate, triethyl citrate, triolein, and a combination of two or more thereof.

16. Buffered aqueous colchicine solution or suspension of claim 15, wherein the ratio of the water-miscible organic solvent with glycerol is 1-5:10 glycerol.

17. Buffered aqueous colchicine solution or suspension of claim 1, comprising 0.05-0.2 w/v % flavouring agent.

18. Buffered aqueous colchicine solution or suspension of claim 17, wherein the flavouring agent is selected from the group consisting of forest fruits flavour, grapefruit, orange, lime, lemon, mandarin, pineapple, strawberry, raspberry, mango, passion fruit, kiwi, apple, pear, peach, apricot, cherry, grapes, banana, cranberry, blueberry, black currant, red currant, gooseberry, lingonberries, cumin, thyme, basil, chamomile, valerian, fennel, parsley, camomile, tarragon, lavender, dill, bergamot, *salvia*, aloe vera balsam, spearmint, peppermint, eucalyptus, and combinations of two or more thereof.

19. Buffered aqueous colchicine solution or suspension of claim 1, wherein the solution or suspension comprises at least 95% colchicine after 24 months storage at 25° C. at a relative humidity of 60% as compared to the amount of colchicine at the beginning of the storage.

20. Buffered aqueous colchicine solution or suspension of claim 1, wherein the solution or suspension comprises less than 3% total impurities after 24 months storage at 25° C. at a relative humidity of 60%.

21. Buffered aqueous colchicine solution or suspension of claim 15, wherein the water miscible organic solvent is selected from the group consisting of alkane triols, alkane diols, polyethylene glycol, ethanol, isopropyl alcohol, acetone, dibutyl phthalate, diethyl phthalate, dimethyl phthalate, dimethyl sulfoxide, dimethylacetamide, glycofurol, isopropyl myristate, isopropyl palmitate, propylene carbonate, pyrrolidine, glycerine triacetate, triethyl citrate, triolein, and a combination of two or more thereof.

* * * * *